United States Patent
Lee et al.

(10) Patent No.: US 9,103,773 B2
(45) Date of Patent: Aug. 11, 2015

(54) CAPACITIVE ELEMENT SENSOR AND METHOD FOR MANUFACTURING SAME

(75) Inventors: Jung Hoon Lee, Seoul (KR); Jun Kyu Choi, Gyeongbuk (KR); Su Jin Lee, Gyeonggi-do (KR); Sung Jun Lee, Gyeongsangnam-do (KR)

(73) Assignee: Seoul National University R&D Foundation, Seoul (KR)

( * ) Notice: Subject to any disclaimer, the term of this patent is extended or adjusted under 35 U.S.C. 154(b) by 357 days.

(21) Appl. No.: 13/696,476

(22) PCT Filed: May 6, 2010

(86) PCT No.: PCT/KR2010/002883
§ 371 (c)(1),
(2), (4) Date: Nov. 6, 2012

(87) PCT Pub. No.: WO2011/138985
PCT Pub. Date: Nov. 10, 2011

(65) Prior Publication Data
US 2013/0057304 A1     Mar. 7, 2013

(51) Int. Cl.
*G01R 27/26* (2006.01)
*G01N 27/327* (2006.01)

(52) U.S. Cl.
CPC ................................. *G01N 27/3276* (2013.01)

(58) Field of Classification Search
CPC .................................................. G01N 27/3276
USPC ................................................. 324/658–690
See application file for complete search history.

(56) References Cited

U.S. PATENT DOCUMENTS

| | | | |
|---|---|---|---|
| 4,238,757 | A | 12/1980 | Schenck |
| 5,466,348 | A | 11/1995 | Holm-Kennedy |
| 6,133,046 | A | 10/2000 | Clerc |
| 6,203,981 | B1 | 3/2001 | Ackley et al. |
| 6,809,527 | B2 | 10/2004 | Ishio et al. |
| 7,387,024 | B2 | 6/2008 | Itakura et al. |
| 2003/0011384 | A1 | 1/2003 | Ishio et al. |
| 2005/0188764 | A1 | 9/2005 | Itakura et al. |
| 2006/0049836 | A1* | 3/2006 | Morimoto et al. ............ 324/661 |
| 2007/0151848 | A1* | 7/2007 | Novak et al. ................... 204/412 |
| 2007/0153141 | A1* | 7/2007 | Tsai et al. ........................ 349/38 |

FOREIGN PATENT DOCUMENTS

| | | |
|---|---|---|
| JP | 63-501446 A | 6/1988 |
| JP | 2001-507454 A | 6/2001 |
| JP | 2003-028825 A | 1/2003 |
| JP | 2005-527799 A | 9/2005 |
| JP | 2005-533482 A | 11/2005 |
| JP | 03994975 B2 | 10/2007 |
| JP | 2008-505044 A | 2/2008 |
| KR | 10-0670018 B1 | 1/2007 |
| KR | 10-2010-0040196 A | 4/2010 |
| KR | 10-2010-0040197 A | 4/2010 |

* cited by examiner

*Primary Examiner* — Jermele M Hollington
*Assistant Examiner* — Farhana Hoque
(74) *Attorney, Agent, or Firm* — Rabin & Berdo P.C.

(57) ABSTRACT

The present disclosure relates to a capacitive element sensor and to a method for manufacturing same. More particularly, the present disclosure relates to a change in total capacitance brought about by the electrical charge of biomolecules attached to an electrode and to a sensor for measuring the change.

2 Claims, 4 Drawing Sheets

ND METHOD FOR MANUFACTURING SAME

CAPACITIVE ELEMENT SENSOR AND METHOD FOR MANUFACTURING SAME

TECHNICAL FIELD

The present disclosure relates to a capacitive element sensor and to a method for manufacturing same. More particularly, the present disclosure relates to a change in total capacitance brought about by the electrical charge of biomolecules attached to an electrode and to a sensor for measuring the change.

BACKGROUND ART

Among sensors designed to detect biomolecules using an electrical signal, there is a TR-based biosensor having a transistor structure. The biosensor is manufactured through a semiconductor manufacturing process and has advantages in that the electrical signal is quickly converted and integration of ICs and MEMS is easy.

Detection of a biological reaction using a field-effect transistor (FET) is disclosed in U.S. Pat. No. 4,238,757 (1980). This patent relates to a biosensor for detecting proteins which detects an antigen-antibody reaction by measuring a current resulting from a change in a semiconductor inversion layer due to variation of surface charge concentration.

U.S. Pat. Nos. 5,466,348 and 6,203,981 disclose improvement of signal-to-noise ratio (S/N) using a thin-film transistor (TFT).

FIG. 1 is a cross-sectional view of a typical bio-FET according to the existing art. A source 112a and a drain 112b are formed on both sides of an n-type or p-type doped substrate 111. A gate 113 is formed on the substrate 111 to be in contact with the source and the drain. The gate 113 generally includes an oxide layer 114, a polysilicon layer 115 and a gate electrode layer 116, and probe biomolecules 117 are attached to the gate electrode layer 116. The probe biomolecules 117 are bound to target biomolecules via, e.g., hydrogen bonding. The binding between the probe biomolecules 117 and the target biomolecules is detected by measuring change in current via an electrical method.

However, the method described above is problematic in that charged biomolecules cannot be detected with reliable accuracy and reproducibility in an electrolyte solution 200.

And, the FET-based biosensor is disadvantageous in that the associated semiconductor manufacturing process is very complicated.

DISCLOSURE

Technical Problem

The present disclosure is directed to providing a capacitive element sensor capable of replacing a thin-film transistor (TFT)-based biosensor.

In particular, the disclosure is directed to providing a capacitive element sensor which is more reliable than a field-effect transistor (FET)-based biosensor.

Technical Solution

To solve the technical problems described above, the present disclosure provides the followings.

In an aspect, the present disclosure provides a method for manufacturing a capacitive element sensor comprising a first electrode, a second electrode and a third electrode separated by a dielectric layer and measuring change in capacitance brought about by the electrical charge of biomolecules attached to the third electrode with the first electrode and the second electrode, which comprises: forming the first electrode and the second electrode on a substrate to be spaced apart from each other; forming the dielectric layer on the first electrode and the second electrode; forming the third electrode on the dielectric layer; and surface-treating the third electrode so that specific biomolecules can be attached thereto.

In another aspect, the present disclosure provides a method for manufacturing a capacitive element sensor comprising a first capacitive element comprising a first electrode, a second electrode and a third electrode separated by a dielectric layer and a second capacitive element comprising a fourth electrode and a fifth electrode provided on the same plane as the first electrode and the second electrode and separated by the dielectric layer and measuring change in a ratio of the capacitance of the first capacitive element to the capacitance of the second capacitive element brought about by the electrical charge of biomolecules attached to the third electrode, which comprises: forming the first electrode, the second electrode, the fourth electrode and the fifth electrode on a substrate to be spaced apart from each other; forming the dielectric layer on the first electrode, the second electrode, the fourth electrode and the fifth electrode; forming the third electrode on the dielectric layer; and surface-treating the third electrode so that specific biomolecules can be attached thereto.

The substrate may be a flexible substrate and roughness may be formed on the opposing surfaces of the first electrode, the second electrode and the third electrode so as to increase surface area.

In another aspect, the present disclosure provides a capacitive element sensor comprising a first electrode, a second electrode separated from the first electrode by a dielectric layer and a third electrode surface-treated so that specific biomolecules can be attached thereto, wherein the first electrode, the second electrode and the third electrode function as capacitive element and change in capacitance brought about by the electrical charge of biomolecules attached to the third electrode is measured with respect to the first electrode and the second electrode.

In another aspect, the present disclosure provides a capacitive element sensor comprising a first electrode, a second electrode separated from the first electrode by a dielectric layer, a third electrode surface-treated so that specific biomolecules can be attached thereto and a fourth electrode and a fifth electrode provided on the same plane as the first electrode and the second electrode and separated from each other, wherein the first electrode, the second electrode and the third electrode form a first capacitive element, the fourth electrode and the fifth electrode form a second capacitive element and change in the capacitance of the first capacitive element and the second capacitive element brought about by the electrical charge of biomolecules attached to the third electrode is measured.

Advantageous Effects

Since the manufacturing process according to the present disclosure is simple as compared to that of a field-effect transistor (FET)-based biosensor, the present disclosure provides an advantageous effect of reducing manufacturing cost. Further, the present disclosure provides an effect of improving detection reliability.

BEST MODE

Hereinafter, the embodiments of the present disclosure will be described in detail with reference to accompanying drawings. The embodiments described below are for illustrative purpose only and the scope of the present disclosure is not limited thereto. The present disclosure may be embodied in various manners within the scope of the present disclosure.

In the following description, details of well-known features and techniques will be omitted to avoid unnecessarily obscuring the presented embodiments.

The terms used below are selected considering their functions in the present disclosure. Since they may be interpreted differently depending on the intention of experimenters, measurers or users and practice, definition should be given based on the overall contents of the present disclosure.

Embodiment 1

Figure 1:
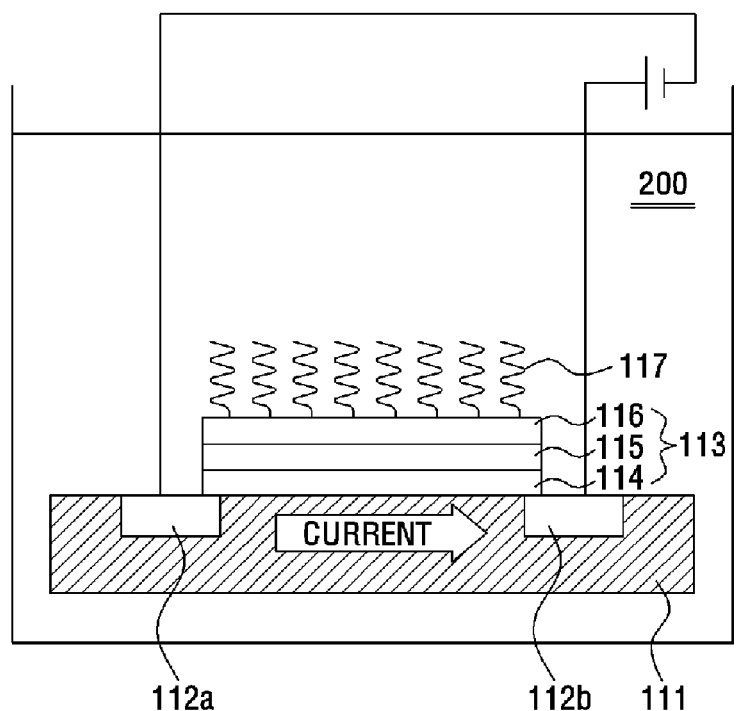
FIG. 1 shows a configuration of an existing field-effect transistor (FET)-based biosensor.
Figure 2:
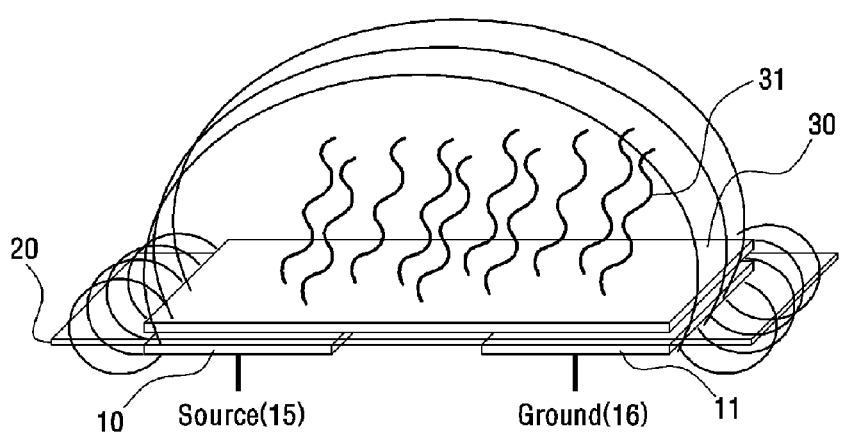
FIG. 2 shows a configuration of a capacitive element sensor according to the present disclosure.

FIG. 2 shows a main configuration of a capacitive element sensor. It is to be noted that, as used herein, the term "capacitive" mainly means capacitance but does not exclude inductance.

Figure 3:
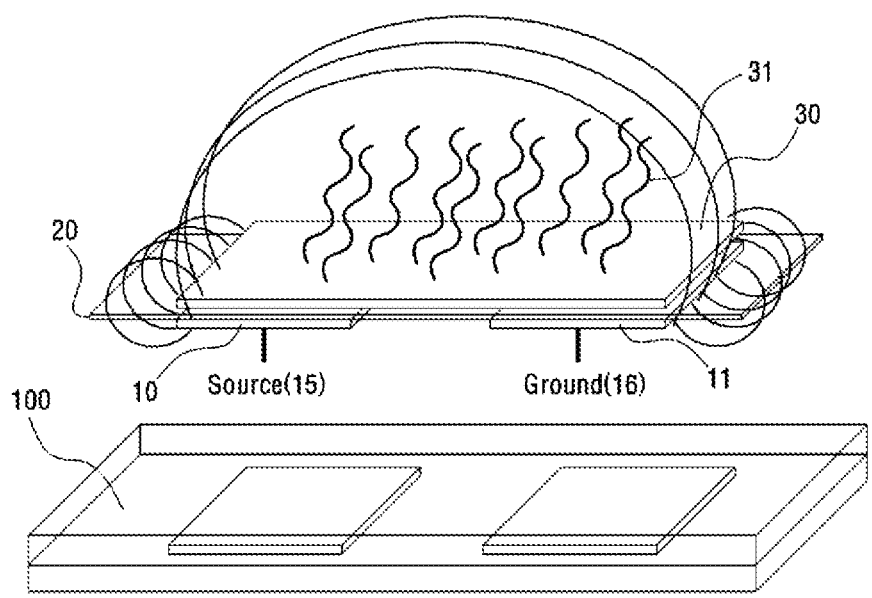
FIG. 3 shows a configuration of a capacitive element sensor according to the present disclosure.

In FIG. 2 and FIG. 3, electric field is depicted as solid lines between electrodes. In particular, the round solid lines between a first electrode 10 and a third electrode 30 and between a second electrode 11 and the third electrode 30 represent fringing electric fields.

A capacitive element sensor according to the present disclosure comprises a first electrode 10, a second electrode 11 separated from the first electrode 10 by a dielectric layer 20 and a third electrode 30 surface-treated so that specific biomolecules can be attached thereto.

The first electrode 10, the second electrode 11 and the third electrode 30 function as a capacitive element. That is to say, the first electrode 10, the second electrode 11 and the third electrode 30 are separated by the dielectric layer 20. Accordingly, the first electrode 10 and the second electrode 11 form a first capacitor, the second electrode 11 and the third electrode 30 form a second capacitor, and the third electrode 30 and the first electrode 10 form a third capacitor.

In particular, if the first electrode 10 is used as a source (+ electrode) and the second electrode 11 is grounded (– electrode), it is equivalent to a circuit wherein the third capacitor and the second capacitor are connected in series and the first capacitor is connected in parallel therewith. That is to say, when a voltage is applied between the first electrode 10 and the second electrode 11 from an external power source, it may be represented by the equivalent circuit described above. The voltage may be AC voltage. In particular, when an AC voltage is applied, an electric field is generated between the first electrode 10 and the third electrode 30 and between the third electrode 30 and the second electrode 11 and they serve as capacitors because of the dielectric layer between the electrodes. As a result, an induced current or an induced voltage is generated at the third electrode.

This circuit may be represented by a total capacitance value which varies as the capacitance of the third capacitor and the second capacitor changes.

As shown in FIG. 3, the first electrode 10 and the second electrode 11 of the capacitive element sensor according to the present disclosure are usually connected to a CMOS chip 100 for measurement of capacitance. But, other configuration is also possible as long as the capacitance of the capacitive element sensor may be measured using the first electrode 10 and the second electrode 11.

Change in current or voltage brought about by the electrical charge of biomolecules attached to the third electrode 30 results in change the capacitance of the second capacitor and the third capacitor, finally resulting in change of the total capacitance. The amount of the biomolecules attached to the third electrode 30 may be measured by measuring the change in capacitance. In general, the biomolecules are negatively charged.

Accordingly, the third electrode 30 may be surface-treated 31 so that specific biomolecules to be tested can be easily attached thereto.

The third electrode 30 may be provided in an electrolyte solution. Alternatively, a test solution may be dropped on the third electrode 30.

It is to be noted that the present disclosure is based on entirely different configuration and principle as compared to the existing field-effect transistor (FET)-based biosensor. That is to say, the present disclosure is technically entirely different from the FET-based biosensor in that an AC voltage is applied between the first electrode 10 and the second electrode 11 and the total capacitance of the circuit is measured.

Specifically, the first electrode 10 and the second electrode 11 used in the present disclosure may comprise a conductive metal such as gold, silver, platinum, copper, aluminum, etc., but the scope of the present disclosure is not limited thereto. For binding with biomolecules, the third electrode 30 may comprise gold (Au). The electrodes may be fabricated by sputtering, electroplating, chemical vapor deposition (CVD), or the like.

Hereinafter, a method for manufacturing the capacitive element sensor according to the present disclosure will be described.

Figure 4:
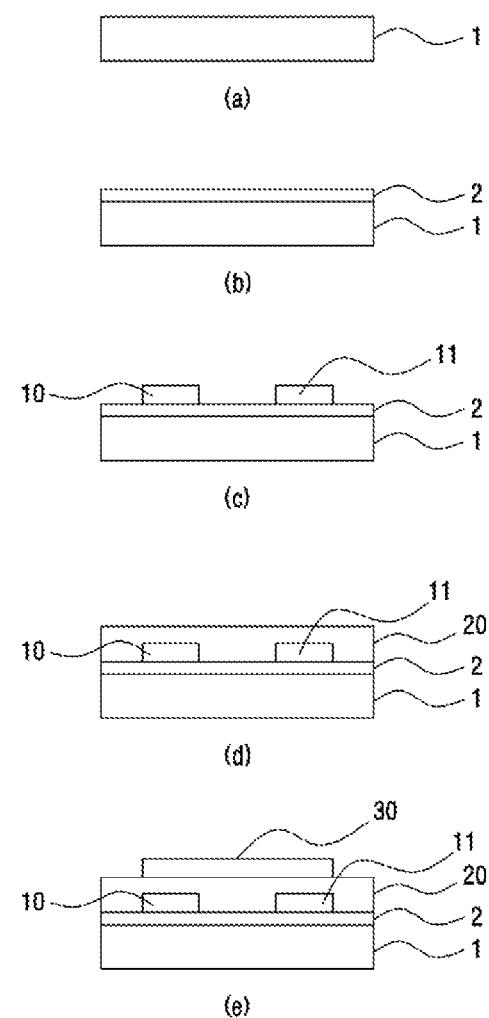
FIG. 4 shows a manufacturing process of a capacitive element sensor according to the present disclosure.

Referring to FIG. 4, the process from (a) to (b) describes a step wherein an oxide layer 2 is formed on a substrate 1.

The substrate 1 used in the capacitive element sensor of the present disclosure may be a glass substrate, a plastic substrate, a silicon substrate, or the like. In particular, it may be a flexible substrate comprising a polymer material such as PDMS.

As for the existing FET-based biosensor, it is impossible to use a flexible substrate because it uses a semiconductor device. In contrast, the capacitive element sensor according to the present disclosure can be embodied on a flexible substrate and is useful since the thickness is small.

When a silicon substrate is used, the oxide layer 2 should be formed on the substrate. For example, the oxide layer 2 may be formed on the substrate by wet oxidation to a thick of 2000 Å using silicon oxide. It is not easy to form a polycrystalline silicon structure on bare surface of the silicon wafer. The oxide layer 2 may also serve as an insulating layer depending on situations.

The process from (b) to (c) describes a step wherein the first electrode 10 and the second electrode 11 are formed on the substrate 1 or the oxide layer 2.

As described earlier, the first electrode 10 and the second electrode 11 may be fabricated by sputtering, electroplating, CVD, or the like. Also, various materials may be used. The materials are selected considering, for example, the means 31 for fixing the biomolecules. For example, if the biomolecules are to be fixed on the electrode via gold-sulfur coordination, gold, silver, platinum or copper may be used.

The process from (c) to (d) describes a step wherein the dielectric layer 20 is formed on the substrate and the electrodes.

In general, the dielectric layer 20 is not formed evenly unless a special process is employed. Rather, the position where the electrode is located tends to be higher than the position where it is not located. But, it may be preferred that the dielectric layer is formed completely evenly on the first electrode 10 and the second electrode 11.

The process from (d) to (e) describes a step wherein the third electrode 30 is formed on the dielectric layer 20. Specifically, the size and location of the third electrode may be determined such that it opposes the first electrode 10 and the second electrode 11 and covers the area of the first electrode 10 and the second electrode 11, but the scope of the present disclosure is not limited thereto.

Since the change in capacitance between the electrodes is measured in the present disclosure, accuracy and reliability may be improved as the capacitance is larger. Accordingly, the area of the opposing electrodes may be increased to improve the accuracy and reliability of the present disclosure.

If an uneven roughness is provided on the electrode during the formation of the electrode, the capacitance of the capacitor may be increased by maximizing the area of the electrode and, thus, the accuracy of measurement may be improved. As used herein, the roughness means that surface of the electrode is not even but has ups and downs.

An example of forming roughness is described in detail in Korean Patent Application Nos. 2010-0040196 and 2010-0040197.

Further, the third electrode 30 may be surface-treated or a fixing means may be attached thereto so that specific biomolecules can be attached thereto. The surface treatment or the fixing means may be specific for the biomolecules.

As described earlier, the change in the capacitance of the capacitive element brought about by the electrical charge of the biomolecules attached to the third electrode 30 is measured with respect to the first electrode 10 and the second electrode 11 and as a result the kind and amount of the biomolecules attached to the third electrode can be identified.

Figure 5:
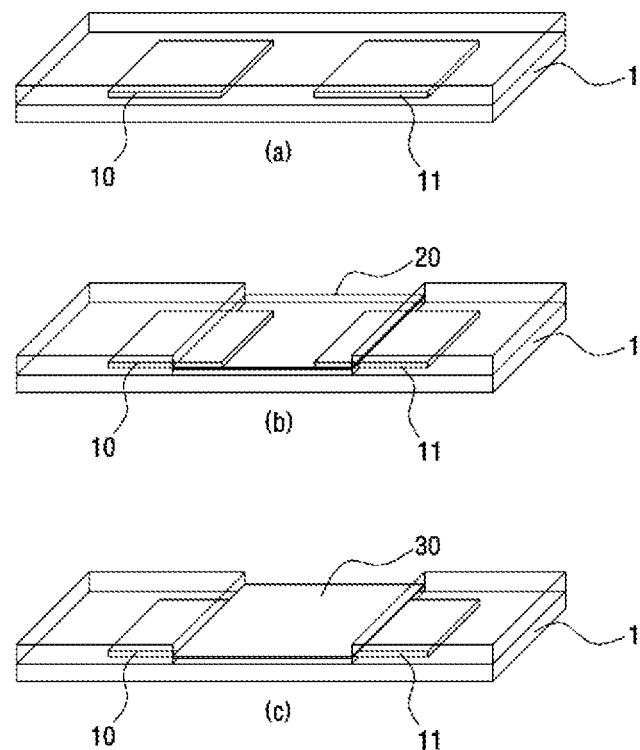
FIG. 5 shows a manufacturing process of a capacitive element sensor according to the present disclosure.

FIG. 5 shows another method for manufacturing the capacitive element sensor of the present disclosure. After the first electrode 10 and the second electrode 11 are formed on the substrate 1, an insulating material is coated thereon.

Then, after the first electrode 10 and the second electrode 11 are partly exposed by etching, the dielectric layer 20 is formed thereon. Then, the third electrode 30 is formed on the dielectric layer 20.

A further detailed description will be omitted since the principle and method are the same as those described above.

Embodiment 2

Figure 6:
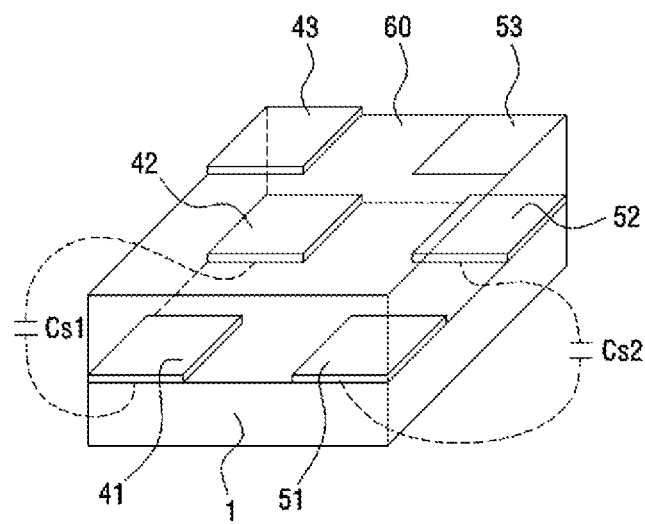
FIG. 6 shows a configuration of a capacitive element sensor according to another embodiment of the present disclosure.

FIG. 6 shows a capacitive element sensor according to another embodiment of the present disclosure.

A first electrode 41 and a second electrode 42 are separated by a dielectric layer 60. A third electrode 43 is surface-treated so that specific biomolecules can be attached thereto. And, a fourth electrode 51 and a fifth electrode 52 are provided on the same plane as the first electrode 41 and the second electrode 42 and separated from each other.

Although it is preferred that the first electrode 41, the second electrode 42, the fourth electrode 51 and the fifth electrode 52 are provided on the same plane, the effect of the present disclosure is not affected even when they are not provided on the same plane.

The first electrode 41, the second electrode 42 and the third electrode 43 form a first capacitive element, and the fourth electrode 51 and the fifth electrode 52 form a second capacitive element.

The difference between the second capacitive element and the first capacitive element is that the second capacitive element lacks an electrode to which the biomolecules are attached.

Total capacitance $C_{s1}$ of the first capacitive element is the sum of the capacitance of the first electrode 41, the second electrode 42 and the third electrode 43, and total capacitance $C_{s2}$ of the second capacitive element is the sum of the capacitance of the fourth electrode 51 and the fifth electrode 52. Although it is shown as if capacitors $C_{s1}$ and $C_{s2}$ are connected to the respective electrodes, it is to be understood as the capacitance of the electrodes.

The operation principle of the first capacitive element is the same as that described with respect to the embodiment 1.

The total capacitance of the first capacitive element changes by the biomolecules attached to the third electrode 43. In contrast, the capacitance of the second capacitive element remains unchanged since it lacks an electrode to which the biomolecules are attached.

Accordingly, the kind and amount of the biomolecules attached to the third electrode 43 can be identified by measuring the change in difference or ratio of the capacitance of the first capacitive element and the capacitance of the second capacitive element.

Although the embodiment 2 is a little more complicated in configuration than the embodiment 1, it enables more accurate detection.

Although the first capacitive element and the second capacitive element are shown to be in proximity in FIG. 6, it is preferred that they are distant from each other as much as possible in order to avoid mutual influence.

The capacitive element sensor according to the embodiment 2 may be manufactured as follows.

The first electrode 41, the second electrode 42, the fourth electrode 51 and the fifth electrode 52 are formed on a substrate 1 to be spaced apart from each other. The dielectric layer 60 is formed on the first electrode 41, the second electrode 42, the fourth electrode 51 and the fifth electrode 52. The third electrode 43 is formed on the dielectric layer 60. Then, the third electrode 43 is surface-treated or a fixing means is attached thereto so that specific biomolecules can be attached thereto.

As described, the present disclosure provides a new-concept biosensor capable of solving the problems of the existing FET-based biosensor. Especially, since the configuration is simple and thickness can be reduced, it is usefully applicable to a flexible substrate.

Further, by surface-treating the electrode to have roughness, detection range and accuracy can be improved by increasing capacitance. In addition, the detection range can be easily adjusted by changing the dielectric material.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

What is claimed is:

1. A capacitive element sensor comprising:
a substrate;
a first electrode formed on the substrate;
a second electrode formed on the substrate and separated from the first electrode;
a dielectric layer formed on the first and second electrodes and the substrate; and
a third electrode formed on the dielectric layer and surface-treated so that specific biomolecules can be attached thereto,
wherein the first electrode and the second electrode are separated by the dielectric layer,
wherein the third electrode includes a lower surface which faces upper surfaces of the first and second electrodes, and roughness is formed on the lower surface of the third electrode and the upper surfaces of the first electrode and second electrode, and
wherein the first electrode, the second electrode and the third electrode function as capacitive element and change in capacitance brought about by the electrical charge of biomolecules attached to the third electrode is measured with respect to the first electrode and the second electrode.

2. The capacitive element sensor according to claim 1, wherein the substrate is a flexible substrate.

* * * * *